(12) United States Patent
Subramaniam et al.

(10) Patent No.: US 9,463,064 B2
(45) Date of Patent: Oct. 11, 2016

(54) ABLATION DEVICE WITH MULTIPLE ABLATION MODES

(71) Applicant: Boston Scientific Scimed Inc., Maple Grove, MN (US)

(72) Inventors: Raj Subramaniam, Fremont, CA (US); Josef V. Koblish, Sunnyvale, CA (US); Zaya Tun, Livermore, CA (US); Guy R. Harvey, Milpitas, CA (US); Minhchau N. Cao, San Jose, CA (US); Kurt D. Sparks, San Carlos, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/846,814

(22) Filed: Sep. 6, 2015

(65) Prior Publication Data

US 2015/0374436 A1    Dec. 31, 2015

Related U.S. Application Data

(62) Division of application No. 13/613,931, filed on Sep. 13, 2012, now Pat. No. 9,125,668.

(60) Provisional application No. 61/534,590, filed on Sep. 14, 2011.

(51) Int. Cl.
*A61B 18/18* (2006.01)
*A61B 18/14* (2006.01)
*A61B 18/00* (2006.01)

(52) U.S. Cl.
CPC .. *A61B 18/1492* (2013.01); *A61B 2018/00023* (2013.01); *A61B 2018/00065* (2013.01); *A61B 2018/00232* (2013.01); *A61B 2018/00238* (2013.01); *A61B 2018/00345* (2013.01); *A61B 2018/00351* (2013.01); *A61B 2018/00577* (2013.01); *A61B 2018/00791* (2013.01);
(Continued)

(58) Field of Classification Search
USPC ............................................................ 606/41
See application file for complete search history.

(56) References Cited

U.S. PATENT DOCUMENTS 3,773,401 A    11/1973    Douklias et al.
4,732,149 A    3/1988    Sutter
(Continued)

FOREIGN PATENT DOCUMENTS

CA    2682055 A1    10/2008
CA    2847846 A1    3/2013
(Continued)

OTHER PUBLICATIONS

Extended European Search Report issued in EP Application No. 15174537.9, issued Mar. 2, 2016, 7 pages.
(Continued)

*Primary Examiner* — Nicole F Lavert
(74) *Attorney, Agent, or Firm* — Faegre Baker Daniels LLP

(57) ABSTRACT

Devices, systems, and methods for performing ablation therapy on body tissue are disclosed. An example ablation device for treating body tissue includes an ionically conductive balloon and a radio-frequency electrode that delivers RF energy into a distal section of the balloon. The balloon is configured to transmit the RF energy in a direction distally towards a leading end of the ablation device. Multiple ablation electrodes on the device can be used for providing lesions of different size or shape.

20 Claims, 9 Drawing Sheets

(52) U.S. Cl.
CPC ............... *A61B2018/00797* (2013.01); *A61B 2018/00815* (2013.01); *A61B 2018/00821* (2013.01); *A61B 2018/00839* (2013.01)

(56) References Cited

U.S. PATENT DOCUMENTS

| | | |
|---|---|---|
| 4,763,660 A | 8/1988 | Kroll et al. |
| 5,029,588 A | 7/1991 | Yock et al. |
| 5,178,150 A | 1/1993 | Silverstein et al. |
| 5,217,460 A | 6/1993 | Knoepfler |
| 5,238,004 A | 8/1993 | Sahatjian et al. |
| 5,240,003 A | 8/1993 | Lancee et al. |
| 5,254,088 A | 10/1993 | Lundquist et al. |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,423,811 A | 6/1995 | Imran et al. |
| 5,447,529 A | 9/1995 | Marchlinski et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,820,568 A | 10/1998 | Willis |
| 5,830,213 A | 11/1998 | Panescu et al. |
| 5,833,621 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,913,856 A | 6/1999 | Chia et al. |
| 5,916,213 A | 6/1999 | Haissaguerre et al. |
| 6,004,269 A | 12/1999 | Crowley et al. |
| 6,027,500 A | 2/2000 | Buckles et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,165,123 A | 12/2000 | Thompson |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,508,803 B1 | 1/2003 | Horikawa et al. |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,547,788 B1 | 4/2003 | Maguire et al. |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,666,862 B2 | 12/2003 | Jain et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,811,550 B2 | 11/2004 | Holland et al. |
| 6,824,517 B2 | 11/2004 | Salgo et al. |
| 6,837,884 B2 | 1/2005 | Woloszko |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,105,122 B2 | 9/2006 | Karason |
| 7,112,198 B2 | 9/2006 | Satake |
| 7,115,122 B1 | 10/2006 | Swanson et al. |
| 7,131,947 B2 | 11/2006 | Demers |
| 7,166,075 B2 | 1/2007 | Varghese et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |

(56) References Cited

U.S. PATENT DOCUMENTS

| | | |
|---|---|---|
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,892,228 B2 | 2/2011 | Landis et al. |
| 7,918,850 B2 | 4/2011 | Govari et al. |
| 8,016,822 B2 | 9/2011 | Swanson |
| 8,048,028 B2 | 11/2011 | Horn et al. |
| 8,128,617 B2 | 3/2012 | Bencini et al. |
| 8,414,579 B2 | 4/2013 | Kim et al. |
| 8,579,889 B2 | 11/2013 | Bencini |
| 8,657,814 B2 | 2/2014 | Werneth et al. |
| 8,740,900 B2 | 6/2014 | Kim et al. |
| 8,771,343 B2 | 7/2014 | Weber et al. |
| 8,894,643 B2 | 11/2014 | Watson et al. |
| 8,945,015 B2 | 2/2015 | Rankin et al. |
| 9,089,340 B2 | 7/2015 | Hastings et al. |
| 9,125,668 B2 | 9/2015 | Subramaniam et al. |
| 9,211,156 B2 | 12/2015 | Kim et al. |
| 2001/0029371 A1 | 10/2001 | Kordis |
| 2002/0087208 A1 | 7/2002 | Koblish et al. |
| 2002/0198521 A1 | 12/2002 | Maguire |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0203597 A1 | 9/2005 | Yamazaki et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0058836 A1 | 3/2008 | Moll et al. |
| 2008/0086073 A1* | 4/2008 | McDaniel ......... A61B 18/1492 604/22 |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312713 A1 | 12/2008 | Wilfley et al. |
| 2009/0030312 A1 | 1/2009 | Hadjicostis |
| 2009/0048591 A1 | 2/2009 | Ibrahim et al. |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0182316 A1 | 7/2009 | Bencini |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0076402 A1 | 3/2010 | Mazzone et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168831 A1 | 7/2010 | Korivi et al. |

(56) References Cited

U.S. PATENT DOCUMENTS

| | | |
|---|---|---|
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2012/0095347 A1 | 4/2012 | Adam et al. |
| 2012/0101398 A1 | 4/2012 | Ramanathan et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0310064 A1 | 12/2012 | McGee |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0172715 A1 | 7/2013 | Just et al. |
| 2013/0172742 A1 | 7/2013 | Rankin et al. |
| 2013/0190747 A1 | 7/2013 | Koblish et al. |
| 2013/0197363 A1 | 8/2013 | Rankin et al. |
| 2013/0274582 A1 | 10/2013 | Afonso et al. |
| 2014/0012251 A1 | 1/2014 | Himmelstein et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0107453 A1 | 4/2014 | Maskara et al. |
| 2014/0107636 A1 | 4/2014 | Bencini |
| 2014/0276052 A1 | 9/2014 | Rankin et al. |
| 2015/0011995 A1 | 1/2015 | Avitall et al. |
| 2015/0133914 A1 | 5/2015 | Koblish |
| 2015/0133920 A1 | 5/2015 | Rankin et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2016/0100884 A1 | 4/2016 | Fay et al. |

FOREIGN PATENT DOCUMENTS

| | | |
|---|---|---|
| CA | 2848053 A1 | 3/2013 |
| CN | 1455655 A | 11/2003 |
| CN | 103917185 A | 7/2014 |
| CN | 103987336 A | 8/2014 |
| CN | 104619259 A | 5/2015 |
| CN | 104640513 A | 5/2015 |
| CN | 104661609 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 1717601 A2 | 11/2006 |
| EP | 1935332 A2 | 6/2008 |
| EP | 2755587 A | 7/2014 |
| EP | 2755588 A | 7/2014 |
| EP | 20136702 B1 | 7/2015 |
| JP | 2000000242 A | 1/2000 |
| JP | 200083918 A | 3/2000 |
| JP | 2000504242 A | 4/2000 |
| JP | 2002528039 A | 8/2002 |
| JP | 2003504090 A | 2/2003 |
| JP | 2004503335 A | 2/2004 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 5336465 B2 | 11/2013 |
| JP | 2014012174 A | 1/2014 |
| JP | 2014531244 A | 11/2014 |
| JP | 2015501162 A | 1/2015 |
| JP | 2015509027 A | 3/2015 |
| KR | 20100021401 A | 2/2010 |
| KR | 101490374 B1 | 2/2015 |
| WO | WO9221278 A1 | 12/1992 |
| WO | WO9413358 A1 | 6/1994 |
| WO | WO97/25917 A1 | 7/1997 |
| WO | WO9725916 A1 | 7/1997 |
| WO | WO97/36541 A1 | 10/1997 |
| WO | 9745156 A2 | 12/1997 |
| WO | WO98/58681 A2 | 12/1998 |
| WO | WO9927862 A1 | 6/1999 |
| WO | WO0029062 A2 | 5/2000 |
| WO | WO0158372 A1 | 8/2001 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO02047569 A1 | 6/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2008118992 A1 | 10/2008 |
| WO | WO2009032421 A2 | 3/2009 |
| WO | 2009043824 A1 | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |
| WO | WO2012001595 A1 | 1/2012 |
| WO | WO2012049621 A1 | 4/2012 |
| WO | WO2012066430 A1 | 5/2012 |
| WO | 2012161880 A1 | 11/2012 |
| WO | 2013040201 A2 | 3/2013 |
| WO | 2013040297 A1 | 3/2013 |
| WO | 2014072879 A2 | 5/2014 |
| WO | 2014152575 A2 | 9/2014 |
| WO | 2015143061 A1 | 9/2015 |
| WO | 2015183635 A1 | 12/2015 |

OTHER PUBLICATIONS

International Preliminary Examination Report issued in PCT/US2013/060612, completed Mar. 24, 2015, 10 pages.
International Preliminary Report on Patentability issued in PCT/US2013/058105, completed Mar. 10, 2015.
International Preliminary Report on Patentability issued in PCT/US2014/027491, mailed Sep. 24, 2015, 12 pages.
International Search Report and Written Opinion issued in PCT/US2013/058105, mailed Nov. 22, 2013, 16 pages.
International Search Report and Written Opinion issued in PCT/US2013/060612, mailed Feb. 28, 2014, 16 pages.
International Search Report and Written Opinion issued in PCT/US2014/027491, mailed Sep. 23, 2014, 17 pages.
International Search Report and Written Opinion issued in PCT/US2015/055173, mailed Jan. 18, 2016, 11 pages.
International Search Report and Written Opinion issued in PCT/US2015/057242, mailed Jan. 15, 2016, 11 pages.
Invitation to Pay Additional Fees and Partial International Search Report issued in PCT/US2014/027491, mailed Jul. 28, 2014, 5 pages.

(56) References Cited

OTHER PUBLICATIONS

Patriciu, A. et al., "Detecting Skin Burns Induced by Surface Electrodes", published in Engineering in Medicine and Biology Society, 2001. Proceedings of the 23rd Annual International Conference of the IEEE, vol. 3, pp. 3129-3131.
Goldberg, S. Nahum et al., "Variables Affecting Proper System Grounding for Radiofrequency Ablation in an Animal Model", JVIR, vol. 11, No. 8, Sep. 2000, pp. 1069-1075.
Haverkamp, W., et. al. Coagulation of Ventricular Myocardium Using Radlofrequency Alternating Current: Bio-Physical Aspects and Experimental Findings. PACE, 12:187-195, Jan. 1989, Part II.
International Preliminary Report on Patentability issued in PCT/US2008/058324, mailed Sep. 29, 2009, 9 pages.
International Preliminary Report on Patentability issued in PCT/US2013/056211, completed Feb. 24, 2015, 5 pages.
International Preliminary Report on Patentablity issued in PCT/US2013/060183, mailed Mar. 24, 2015, 6 pages.
International Search Report and Written Opinion issued in PCT/US2008/058324, dated Aug. 18, 2008, 11 pages
International Search Report and Written Opinion issued in PCT/US2012/031819, mailed Sep. 27, 2012, 16 pages.
International Search Report and Written Opinion issued in PCT/US2012/055309, mailed Nov. 19, 2012, 13 pages.
International Search Report and Written Opinion issued in PCT/US2012/072061, mailed Mar. 21, 2013, 9 pages.
International Search Report and Written Opinion issued in PCT/US2013/020503, mailed Mar. 20, 2013, 10 pages.
International Search Report and Written Opinion issued in PCT/US2013/021013, mailed Apr. 5, 2013, 14 pages.
International Search Report and Written Opinion issued in PCT/US2013/056211, mailed Jan. 20, 2014.
International Search Report and ritten Opinion issued in PCT/US2013/060183, mailed Jan. 27, 2014, 10 pages.
International Search Report and Written Opinion issued in PCT/US2013/060194, mailed Jan. 29, 2014.
International Search Report and Written Opinion issued in PCT/US2013/060194, mailed Jan. 29, 2014, 10 pages.
International Search Report and Written Opinion issued in PCT/US2015/021300, mailed Jun. 9, 2015, 11 pages.
International Search Report and Written Opinion issued in PCTUS2015/031591, mailed Aug. 2015, 11 pages.

Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeid, Gordon R, et al., "Electrical Impedance Properties of the Body and the Problem of Aiternate-site Burns During Electrosurgery", Medical Instrumentation, vol, 19, No. 2, Mar-Apr. 1985, pp. 83-87.
Partial International Search Report issued in PCT/US2012/055155, mailed Dec. 20, 2012, 7 pages.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pines, L. A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mappina Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Ring, E. R., et. al. Catheter Abiation of the Ventricular Septum with Radiofrequency Energy. American Heart journal, 117(6)1233-1240, Jun. 1989.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
Zachary, J.M. et al., "PO4-86 Pin Electrodes Provide Enhanced Resolution Enabling of Radiofrequency Duration to Lesion Maturation", Heart Rhythm 2011, 32 Annual Scientific Sessions, May 4-7, San Francisco, CA.
International Preliminary Report on Patentability issued in PCT/US2012/055155, issued on Mar. 18, 2014, 11 pages.
International Preliminary Report on Patentability issued in PCT/US2012/055309, issued on Mar. 18, 2014, 8 pages.
International Search Report and Written Opinion issued in PCT/US2012/055155, mailed Mar. 11, 2013, 19 pages.

\* cited by examiner

ABLATION DEVICE WITH MULTIPLE ABLATION MODES

CROSS-REFERENCE TO RELATED APPLICATION

This application is a division of U.S. application Ser. No. 13/613,931, filed Sep. 13, 2012, which is now U.S. Pat. No. 9,125,668, issued on Sep. 8, 2015, and claims priority to U.S. Provisional Application No. 61/534,590, filed Sep. 14, 2011, which is herein incorporated by reference in its entirety.

This application is related to U.S. Provisional Application No. 61/534,587, entitled "Ablation Device With Ionically Conductive Balloon," filed on Sep. 14, 2011. The content of this related application is incorporated herein by reference in its entirety for all purposes.

TECHNICAL FIELD

The present disclosure relates generally to an ablation device. More specifically, the present disclosure pertains to an ablation device including an ionically conductive balloon for performing radio-frequency ablation therapy on body tissue.

BACKGROUND

The treatment of cardiac arrhythmias is sometimes performed in conjunction with an ablation catheter inserted into a chamber of the heart or in one of the vessels leading into or from the heart. In the treatment of atrial fibrillation, for example, a radio frequency (RF) ablation catheter equipped with a number of electrodes can be brought into contact with cardiac tissue for creating one or more ablation points along the tissue. During ablation, an RF generator supplies electrical energy to the electrodes, generating an electric field in the tissue. The resulting heat from this electric field forms a controlled lesion that blocks the electrical impulses from being conducted through the tissue and serves to promote the normal conduction of electrical impulses through the proper electrical pathway within the heart.

In certain catheter ablation procedures, it may be difficult to electrically isolate the tissue to be treated. In the treatment of paroxysmal atrial fibrillation, for example, it is often tedious and time consuming to isolate the pulmonary veins using an ablation catheter having an ablation electrode that directly contacts the tissue. Moreover, the ablations created by some ablation electrodes can cause dehydration in the tissue, which can result in scarring and calcification as the lesion heals. Due to the discrete nature of the ablation points, there is also the potential for leaving small gaps of electrically conductive tissue in the ablation line that may continue to initiate points of arrhythmias.

SUMMARY

The present disclosure relates generally to an ablation device including an ionically conductive balloon for performing radio-frequency ablation therapy on body tissue.

In Example 1, an ablation device for treating body tissue, comprises: an elongate shaft having a proximal section, a distal section, and at least one fluid lumen configured to receive an electrically conductive fluid; an inflatable balloon coupled to the distal section of the shaft and including an interior section in fluid communication with the at least one fluid lumen for actuating the balloon between a collapsed state and an expanded state, wherein the balloon comprises a composite structure having a proximal balloon section including a first polymeric material and a distal balloon section including a second polymeric material different from the first material; and at least one electrode located within the interior space of the balloon.

In Example 2, the ablation device according to Example 1, wherein the first polymeric material is a hydrophobic polymer.

In Example 3, the ablation device according to any of Examples 1-2, wherein the second polymeric material is a hydrophilic polymer.

In Example 4, the ablation device according to any of Examples 1-3, further comprising at least one additional fluid lumen for recirculating fluid through the device.

In Example 5, the ablation device of according to any of Examples 1-4, wherein, in the expanded state, the balloon is conically shaped.

In Example 6, the ablation device according to any of Examples 1-5, wherein the distal section of the balloon is invaginated.

In Example 7, the ablation device according to any of Examples 1-6, wherein the distal section of the balloon is semi-permeable.

In Example 8, the ablation device according to any of Examples 1-7, wherein a thickness of the balloon tapers along a length of the balloon from the proximal balloon section to the distal balloon section.

In Example 9, the ablation device according to any of Examples 1-8, wherein the balloon comprises a multi-layered structure.

In Example 10, the ablation device according to any of Examples 1-9, further comprising a temperature sensing element coupled to the distal section of the balloon.

In Example 11, the ablation device according to any of Examples 1-10, further comprising at least one electrocardiogram sensor coupled to the distal section of the balloon.

In Example 12, the ablation device according to any of Examples 1-11, further comprising a spring-actuated plunger assembly configured to bias the balloon in the collapsed state.

In Example 13, the ablation device according to Example 12, wherein the plunger assembly comprises a plunger mechanism and a spring configured to bias the plunger mechanism against the balloon.

In Example 14, the ablation device according to Example 13, wherein the plunger mechanism includes a plunger shaft and an atraumatic tip.

In Example 15, the ablation device according to Example 14, wherein the plunger shaft is slidably disposed within the catheter shaft and the electrode.

In Example 16, an ablation device for treating body tissue comprises: an elongate shaft having a proximal section, a distal section, and at least one fluid lumen configured to receive an electrically conductive fluid; an inflatable balloon coupled to the distal section of the shaft and including an interior section in fluid communication with the at least one fluid lumen for actuating the balloon between a collapsed state and an expanded state; at least one electrode located within the interior space of the balloon; and a spring mechanism configured to bias the balloon in the collapsed state.

In Example 17, a method of forming a balloon of an ablation catheter, the balloon having a proximal section and a distal section, the method comprising: masking the proximal section of the balloon; irradiating the distal section of the balloon with an ionizing radiation source; etching the balloon to form a plurality of micropores through the distal section of the balloon; and securing the balloon to a catheter.

In Example 18, the method according to Example 17, wherein the ionizing radiation source comprises an argon ion source.

In Example 19, the method according to any of Examples 17-18, wherein the proximal section of the balloon comprises a hydrophobic polymer and the distal section of the balloon comprises a hydrophilic polymer.

In Example 20, the method according to any of Examples 17-19, wherein a pore size of the micropores is between about 0.1 microns to 5 microns in diameter.

In Example 21, a system for ablating body tissue comprises: an RF generator including a switching mechanism operable between a first position and a second position; a fluid source including a supply of electrically conductive fluid; and an ablation device, the ablation device including an elongate shaft having a proximal section, a distal section, and at least one fluid lumen; an inflatable balloon coupled to the distal section of the shaft and including an interior section in fluid communication with the fluid source for actuating the balloon between a collapsed state and an expanded state; a first electrode disposed within the interior space of the balloon and electrically coupled to the RF generator, the first electrode configured for supplying a first RF electrical field through the balloon and into the body tissue when operating in the first position; a second electrode coupled to a distal end portion of the elongate shaft and electrically coupled to the RF generator, the second electrode configured for supplying a second RF electric field directly into the tissue when operating in the second position.

In Example 22, the system according to Example 21, wherein the balloon comprises a composite structure having a proximal balloon section including a hydrophobic polymeric material and a distal balloon section including a hydrophilic polymeric material.

In Example 23, the system according to any of Examples 21-22, wherein, in the expanded state, the balloon is conically shaped.

In Example 24, the system according to any of Examples 21-23, wherein the distal section of the balloon is invaginated.

In Example 25, the system according to any of Examples 21-24, wherein the distal section of the balloon is semi-permeable.

In Example 26, the system according to any of Examples 21-25, wherein a thickness of the balloon tapers along a length of the balloon from a proximal balloon section to a distal balloon section.

In Example 27, the system according to any of Examples 21-26, wherein the balloon comprises a multi-layered structure.

In Example 28, the system according to any of Examples 21-27, further comprising a spring-actuated plunger assembly configured to bias the balloon in the collapsed state.

In Example 29, a method for performing ablation therapy on the body of a patient comprises: advancing an ablation device to a target body tissue region, the ablation device including an inflatable balloon coupled to an elongate shaft, a first electrode disposed within an interior space of the balloon, and a second electrode located outside of the balloon; injecting an electrically conductive fluid into the interior section of the balloon and inflating the balloon from a collapsed state to an expanded state within the body; selectively energizing the first electrode and generating a first RF electrical field within the balloon interior; forming at least one ablation lesion within the body tissue using the first RF electrical field; selectively energizing the second electrode and generating a second RF electrical field; and forming at least one ablation lesion within the body tissue using the second RF electrical field.

In Example 30, the method according to Example 29, further comprising an RF generator including a switching mechanism, and wherein selectively energizing the first or second electrodes includes operating the switching mechanism between a first and second switch position.

In Example 31, the method according to any of Examples 29-30, wherein forming at least one ablation lesion within the body tissue using the first RF electrical field includes forming a lesion in the body tissue at a location distal to the elongate shaft.

In Example 32, the method according to any of Examples 29-31, wherein the at least one ablation lesion formed within the body tissue using the first RF electric field is larger than the at least one ablation lesion formed in the body tissue using the second RF electric field.

In Example 33, an ablation device for treating body tissue comprises: an elongate shaft having a proximal section, a distal section, and at least one fluid lumen configured to receive an electrically conductive fluid; an inflatable balloon coupled to the distal section of the shaft and including an interior section in fluid communication with the at least one fluid lumen for actuating the balloon between a collapsed state and an expanded state; and at least one electrode located within the interior space of the balloon, the at least one electrode configured for transmitting an RF electric field through the balloon and into body tissue in contact with the balloon; wherein the balloon is configured to transmit the RF electric field in a direction distally towards a leading end of the ablation device.

In Example 34, the ablation device according to Example 33, wherein the balloon comprises a composite structure having a proximal balloon section including a hydrophobic polymeric material and a distal balloon section including a hydrophilic polymeric material.

In Example 35, the ablation device according to any of Examples 33-34, wherein, in the expanded state, the balloon is conically shaped.

In Example 36, the ablation device according to any of Examples 33-35, wherein the distal section of the balloon is invaginated.

In Example 37, the ablation device according to any of Examples 33-36, wherein the distal section of the balloon is semi-permeable.

In Example 38, the ablation device according to any of Examples 33-37, wherein a thickness of the balloon tapers along a length of the balloon from a proximal balloon section to a distal balloon section.

In Example 39, the ablation device according to any of Examples 33-38, wherein the balloon comprises a multi-layered structure.

In Example 40, the ablation device according to any of Examples 33-39, further comprising a spring-actuated plunger assembly configured to bias the balloon in the collapsed state.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
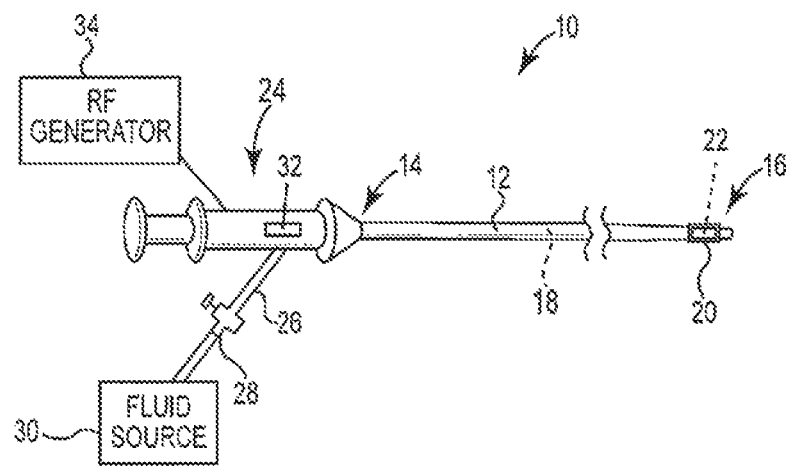
FIG. 1 is a schematic view of an ablation device in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an ablation device 10 in accordance with an illustrative embodiment. As shown in FIG. 1, the ablation device 10 includes an elongate shaft 12 having a proximal section 14, a distal section 16, and at least one lumen 18 extending through the shaft 12 between the proximal and distal sections 14, 16. An inflatable ablation balloon 20 coupled to the distal section 16 of the shaft 12 can be inflated at a target location within the body (e.g., within a cardiac vessel) and brought into contact with the body tissue to be treated. In some embodiments, and as further described below, an RF electrode assembly 22 located within an interior portion of the balloon 20 generates an RF electric field that can be used for creating controlled lesions within the tissue. In the treatment of paroxysmal atrial fibrillation, for example, the balloon 20 and RF electrode 22 can be used for performing electrical isolation within a pulmonary vein to prevent the aberrant conduction of electrical signals within the left side of the heart. The ablation device 10 can also be used for treating other types of cardiac arrhythmias and/or cardiovascular diseases within the body. The ablation device 10 can also be used for treating other conditions commonly performed by ablation devices.

A handle 24 coupled to the proximal section 14 of the shaft 12 can be used by the clinician for manipulating and steering the distal section 16 to a target site within the body for performing an ablation. In some embodiments, the handle 24 includes a fluid port 26 and valve 28 in fluid communication with a source of electrically conductive fluid 30. In some embodiments, for example, the fluid 30 can comprise saline or a solution of saline and a fluoroscopic contrast medium that is both conductive and biocompatible. During an ablation procedure, pressurized fluid 30 can be delivered via the fluid lumen 18 to the interior of the balloon 20, causing the balloon 20 to inflate while also creating an electrical pathway between the electrode 22 and the portion of the balloon 20 in contact with the body tissue to be treated. In some embodiments, multiple fluid ports can be provided to recirculate the fluid 30 through the ablation device 10 as part of a closed-loop system for controlling the temperature within the balloon 20.

In some embodiments, the ablation device 10 further includes a steering mechanism 32 that can be used to mechanically steer the distal section 16 of the shaft 12 within the body. In certain embodiments, for example, the steering mechanism 32 comprises a slider or lever mechanism on the handle 24 that can be actuated by the clinician to engage a number of steering wires located within the shaft 12. During delivery of the device 10 to a target region within the body, the steering mechanism 32 can be engaged to deflect the distal section 16 of the shaft 12, allowing the clinician to better navigate the device 10 through the vasculature.

An RF generator 34 is configured to supply radio-frequency energy to the electrode assembly 22. In some embodiments, the device 10 is configured to operate in a bipolar mode, in which ablation energy supplied by the RF generator 34 flows from one electrode of the electrode assembly 22 to another electrode of the electrode assembly 22 or provided at a different location along the device 10 (e.g., along the distal section 16 of the shaft 12). In other embodiments, the device 10 is configured to operate in a unipolar mode, in which an indifferent electrode (e.g., an electrode patch) is attached to the patient's back or other exterior skin area and ablation energy from the RF generator 34 flows from one electrode of the assembly 22 to the indifferent electrode.

Figure 2:
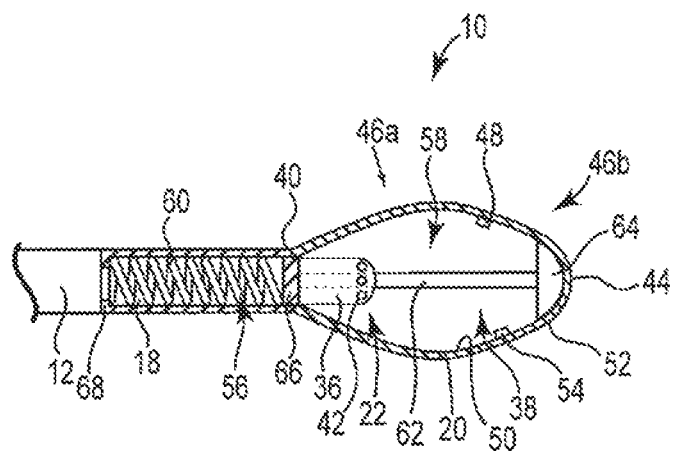
FIG. 2 is a partial cross-sectional view showing the distal section of the ablation device of FIG. 1 in a collapsed state.

FIG. 2 is a partial cross-sectional view showing the distal section 16 of the ablation device 10 of FIG. 1 in greater detail. As can be further seen in FIG. 2, and in some embodiments, the electrode assembly 22 comprises at least one RF electrode 36 located within an interior space 38 of the balloon 20. The RF electrode 36 is fixedly secured to a distal end 40 of the shaft 12 (e.g., using a suitable adhesive at both ends of the electrode 36), and is electrically coupled to the RF generator 34. In the embodiment of FIG. 2, the RF electrode 36 comprises a metal tubular member made from a suitably conductive metal such as platinum, and is electrically coupled to the RF generator 34 via a number of conductor wires (not shown) located within the shaft 12. The configuration of the RF electrode 36 can vary from that shown, however. For example, the RF electrode 36 can comprise a coil, ring, flat ribbon, or other suitable shape. In some embodiments, the electrode assembly 22 can include multiple electrodes 36 as part of either a bipolar RF ablation system, or as part of a unipolar system with multiple electrodes.

The device 10 includes at least one fluid lumen for transmitting pressurized fluid 30 to the interior space 38 of the balloon 20. In the embodiment of FIG. 2, the device 10 includes a central fluid lumen 18 that extends longitudinally through the shaft 12 and through a portion of the RF electrode 36. In some embodiments, the fluid lumen 18 terminates distally at a number of inflation ports 42 disposed circumferentially about the RF electrode 36. In some embodiments, the same fluid lumen 18 can be used for both inflating and deflating the balloon 20. In other embodiments, separate fluid lumens are used for inflating and deflating the balloon 20. Such a configuration can provide continuous infusion and evacuation of fluid within the balloon 20 to maintain both a controlled operating pressure and temperature within the balloon 20. In one embodiment, multiple fluid lumens within the shaft 12 may permit the electrically conductive fluid 30 to be recirculated through the device 10 during the ablation procedure. The fluid 30 can also include a contrast medium to facilitate visualization of the balloon 20 under fluoroscopy.

In the embodiment of FIG. 2, the balloon 20 is coupled to the distal section 16 of the shaft 12 at or near the distal shaft end 40, and is inflatable from an initial, collapsed position having a low-profile that facilitates traversal of the device 10 through the body, to a second, expanded position that contacts and engages the body tissue to be ablated. In certain embodiments, the balloon 20 has a composite structure formed from different polymeric materials, which helps to direct and focus the RF energy from the RF electrode 36 into the body tissue located at or near a distal end 44 of the balloon 20. In one embodiment, for example, the composite balloon 20 includes a proximal, non-conductive section 46a made from a hydrophobic polymer and a distal, conductive section 46b made from a hydrophilic polymer. The polymer of the non-conductive section 46a can be non-ionically conductive and the polymer of the distal section 46b can be ionically conductive. In some embodiments, for example, the composite balloon structure can comprise a proximal section 46a made from a hydrophobic polyurethane material such as TECOPHILIC 60D-35® and a distal section 46b made from a hydrophilic polyurethane material such as TECOPHILIC 60D®, both of which are available from Thermedics Polymer Products of Woburn, Mass. TECOPHILIC® is a polyether-based aliphatic polyurethane and exhibits sufficient elasticity so as to be capable of stretching substantially beyond its equilibrium dimensions when the balloon 20 is inflated. Other polymeric materials can also be used to impart differing hydrophilic characteristics to the proximal and distal sections 46a, 46b. As used herein, the term "hydrophilic" indicates that the polymer, when in contact with an aqueous solution, can absorb a quantity of water while still maintaining its structural integrity.

When inflated with the electrically conductive fluid 30, the distal section 46b of the composite balloon 20 is rendered conductive by hydration due to the ionic content of the fluid 30 when the RF energy is supplied to the RF electrode 36. As a result, electrical current is transmitted through the fluid 30 and into the tissue in contact with the distal section 46b of the balloon 20. In some cases, current passes through all areas of the balloon material that are hydrophilic but does not pass through areas of the balloon that are hydrophobic or non-conductive.

The composite balloon structure can be formed using a number of different techniques. For example, the different sections 46a, 46b of the balloon 20 can be formed by separately dip-coating each section of the balloon 20 on a mandrel that has a defined size and shape. The balloon 20 can also be formed using other techniques, such as by spin-coating in a hollow mold or by injection or blow-molding. Another example method for constructing a composite balloon structure having a permeable or semi-permeable distal section is discussed further herein with respect to FIG. 4.

In some embodiments, the device 10 further includes one or more temperature sensing elements that can be used to sense the temperature of fluid 30 within the balloon 20. In certain embodiments, and as shown in FIG. 2, a temperature sensing element 48 such as a thermocouple or thermistor is coupled to the inner surface 50 of the balloon 20 at the distal section 46b. In other embodiments, the temperature sensing element 48 is coupled to an outer surface 52 of the balloon 20 at the distal section 48, or is coupled to another portion of the balloon 20 or to the shaft 12. In another embodiment, the temperature sensing element 48 is encased within the interior of the balloon material. In some embodiments, multiple temperature sensing elements can be coupled to the inner and/or outer surfaces 50, 52 of the balloon and/or to the shaft 12 for sensing temperature at multiple locations.

In some embodiments, the temperature sensing element 48 senses the temperature of the fluid 30 contained within the interior section 38 of the balloon 20, and is connected to temperature sensing circuitry (e.g., based on a thermometer) located outside of the body. During ablation, the RF generator 34 can be controlled so as to adjust the temperature of the fluid 30 contained in the balloon 20 to a desired temperature. In those embodiments in which multiple fluid ports are utilized for recirculating fluid through the device 10, the flow of fluid can also be controlled based on feedback from the temperature sensing element 48 to maintain the fluid within the balloon 20 at a particular temperature or within a range of temperatures. In various embodiments, a temperature sensor is located on the outer surface of the balloon and/or within the wall of the balloon. Such a configuration can measure the temperature of the tissue undergoing ablation. In these or other embodiments referenced herein, the intensity of ablation therapy (e.g., power) can be automatically modulated based on the measured temperature to limit the temperature of the tissue undergoing ablation. Such a configuration can provide protection from steam pops, where a small gaseous rupture in tissue can otherwise be created by water in the tissue turning into steam when the temperature reaches 100° C. or greater.

One or more electrocardiogram sensors coupled to the balloon 20 can also be used in some embodiments for sensing electrical activity in or near the heart. In the embodiment of FIG. 2, for example, an electrocardiogram sensor 54 is coupled to the inner surface 50 of the balloon 20 at the distal section 46b, allowing the clinician to monitor for the presence of any electrical activity at the target ablation site. In other embodiments, the electrocardiogram sensor 54 is coupled to the outer surface 52 of the balloon 20 at the distal section 46, or is coupled to another portion of the balloon 20 or shaft 12. In another embodiment, the electrocardiogram sensor 52 is encased within the interior of the balloon material. In some embodiments, multiple electrocardiogram sensors can be coupled to and/or encased within the balloon 20 and/or to the shaft 12 for sensing electrical activity at multiple locations.

A spring actuated plunger assembly 56 can be used to maintain the balloon 20 in a collapsed, low-profile position to facilitate delivery of the device 10 through the body prior to inflating the balloon 20 at the desired target tissue location. In the embodiment of FIG. 2, the assembly 56 includes a plunger mechanism 58 and a spring 60. The spring 60 is located within the interior of the shaft 12 proximal to the RF electrode 36, and is configured to mechanically bias the plunger mechanism 58 in a distal direction towards the distal end 44 of the balloon 20, thus maintaining the balloon 20 in an extended position until inflated.

In some embodiments, the plunger mechanism 58 comprises a plunger shaft 62 slidably disposed within the interior section 38 of the balloon 20 and through a portion of the RF electrode 36. The distal end of the plunger shaft 62 includes an atraumatic tip 64 which, when the plunger mechanism 58 is fully engaged distally, is configured to contact and engage the distal end 44 of the balloon 20 causing the balloon 20 to collapse and assume a low-profile position, as shown. The shape of the tip 64 is curved to conform to the shape of the balloon 20 at the distal end 44. The proximal end of the plunger shaft 62 is coupled to a plunger seal 66, which provides a surface against which the spring 60 engages the plunger shaft 62. A shoulder 68 located within the interior of the shaft 12 proximal to the spring 60 provides a proximal stop to prevent proximal movement of the spring 60 when the spring 60 is compressed.

Figure 3:
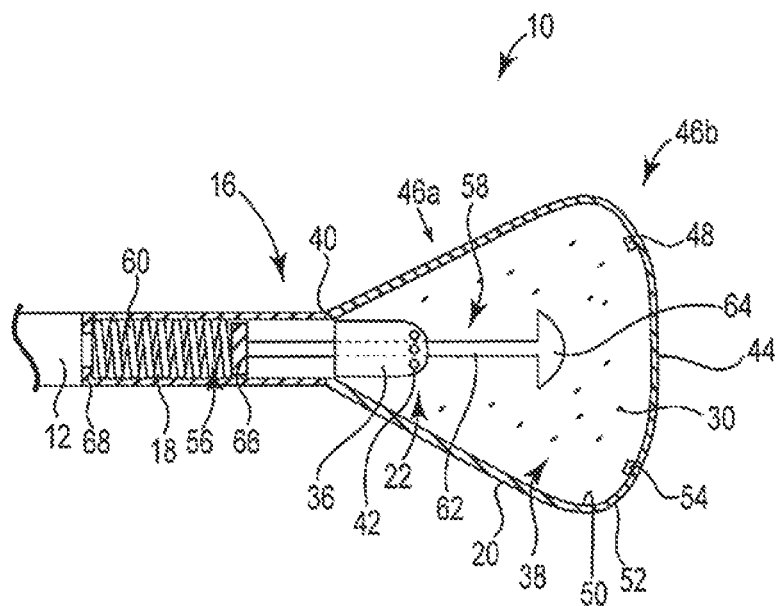
FIG. 3 is another partial cross-sectional view showing the distal section of the ablation device of FIG. 1 in an expanded state.

FIG. 3 is another partial cross-sectional view of the ablation device 10 of FIG. 1, showing the balloon 20 in a second, fully expanded position. As can be further seen in FIG. 3, when pressurized fluid 30 is injected into the interior section 38 of the balloon 20, the fluid pressure exerted against the surface of the plunger seal 66 is configured to overcome the spring bias provided by the spring 60, causing the spring 60 to move to a second, compressed position within the shaft interior. Once the balloon 20 is inflated, the pressure within the interior section 38 of the balloon 20 pushes the plunger assembly 56 in a proximal direction. As a result, the plunger shaft 62 is drawn proximally into the shaft interior, causing the atraumatic tip 64 to disengage from the distal end 44 of the balloon 20.

When the tip 64 disengages from the distal end 44 of the balloon 20, and as shown in FIG. 3, the balloon 20 is configured to expand to its second, expanded position. In some embodiments, the shape of the inflated balloon 20 may vary along its length such that the proximal section 46a of the balloon 20 has a profile and shape that is different from that of the distal section 46b. In the embodiment of FIG. 3, for example, the inflated balloon 20 has a substantially conical shape such that the distal, conductive section 46b of the balloon 20 exposes a relatively large area towards the distal end 44 of the balloon 20. The conical shape of the distal section 46b facilitates contact of the balloon 20 with body tissue located primarily distally of the device 10. The proximal section 46a of the balloon 20, in turn, has a relatively low profile, and thus does not contact the body tissue. In contrast to the distal section 46b, the hydrophobic material of the proximal section 46a also does not conduct with the fluid 30 within the balloon 20.

Although the illustrative balloon 20 in FIG. 3 has a conical shape when expanded, in other embodiments the balloon 20 can have a different shape and/or profile when inflated. Examples of other balloon shapes can include elliptical, spherical, or dumbbell. In some embodiments, the balloon shape can be similar to one of the self-anchoring balloon shapes described in U.S. Pat. No. 7,736,362, the contents of which are incorporated herein by reference in their entirety for all purposes. Other balloon configurations are also possible.

In some embodiments, the distal section 46b of the balloon 20 is semi-permeable, allowing at least some of the pressurized fluid 30 within the interior section 38 of the balloon 20 to seep into the body at or near the target ablation site. In some embodiments, the distal section 46b of the balloon 20 is permeable, allowing the pressurized fluid 30 within the interior section 38 of the balloon 20 to seep into the body at or near the target ablation site. During ablation, the presence of the electrically conductive fluid at this interface region aids in creating an electrical conduit for the electrical field generated by the RF electrode 36, and further serves to cool the ablation site. As the RF energy is applied to the RF electrode 36 inside the balloon 20, the RF energy is transmitted to the tissue in contact with the balloon 20 through the electrically conductive fluid seeping through the balloon 20. The permeability or semi-permeability of the distal section 46b also permits the delivery of an agent or drug contained within the fluid 30. In this manner, the balloon 20 may also act as a drug delivery device by introducing one or more drugs into the conductive fluid 30 and permitting the drugs to pass through the balloon 20 and into the tissue.

Figure 4:
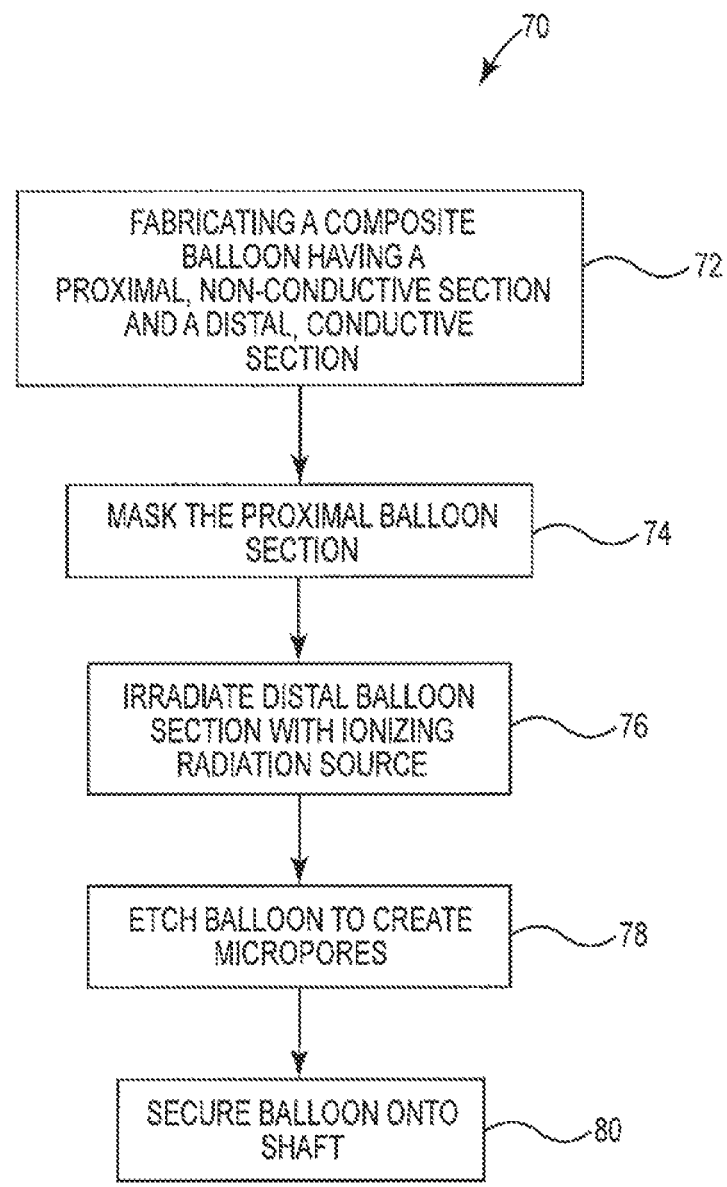
FIG. 4 is a flow diagram showing an example method for fabricating a porous balloon of an ablation device.

FIG. 4 is a flow diagram showing an example method 70 for fabricating a porous balloon. The method 70 may begin generally at block 72, by fabricating a composite balloon having a proximal, non-conductive section and a distal, conductive section. It is noted that in some embodiments the distal section is non-conductive. In certain embodiments, for example, a composite balloon 20 such as that shown in FIGS. 2-3 can be fabricated using a suitable process such as dip-coating, spin-coating, injection molding, or blow-molding. Other fabricating techniques for fabricating a composite balloon can also be utilized.

The balloon material or materials can be selected so as to facilitate further processing steps to create micropores through the balloon material. In some embodiments, for example, the workpiece used to create the composite balloon can be formed from a thermoplastic polymer resin such as polyethylene terephthalate (PET). The thermal and/or chemical characteristics of PET permit subsequent processing steps to be performed on the balloon while maintaining the desired tensile strength and elasticity characteristics of the balloon.

Once the composite balloon has been fabricated, the proximal, non-conductive section of the balloon is masked (block 74), and the distal (e.g., conductive) section of the balloon is irradiated with ions from an ionizing radiation source (block 76). In one embodiment, the composite balloon is irradiated with Argon atoms from an Argon plasma source. Other suitable ionic radiation sources can also be used to irradiate the distal section of the balloon with ions.

Once irradiated, the balloon is then subjected to a sodium hydroxide (NaOH) etching process for a period of time to produce uniform micropores in the distal section of the balloon (block 78). In certain embodiments, for example, the balloon can be inserted into an etching bath and treated for a period of approximately 10 to 15 minutes until pores of a desired size are formed through the balloon material. The pore size can be controlled by the duration of the ionizing radiation and etching steps, the strength of the ionizing radiation, and the strength of the etching solution. Other factors such as the balloon composition, balloon thickness, as well as other characteristics can also affect the pore size. An example pore size that can be generated using this process can be between about 0.1 microns to about 5 microns in diameter, although other pore sizes greater or smaller are also contemplated. For example, in some cases pores can be up to 20 microns in diameter.

Once the micropores are created in the distal section of the balloon, additional processing steps can then be performed to secure the balloon onto the shaft (block 80). In one embodiment, the balloon can be mounted to the distal end of a shaft, similar to that shown in the illustrative embodiment shown in FIGS. 2-3. The balloon can be secured to the shaft in a variety of ways, including adhesive bonding, thermal bonding, mechanical bonding, screws, winding, or a combination of these.

Figure 5:
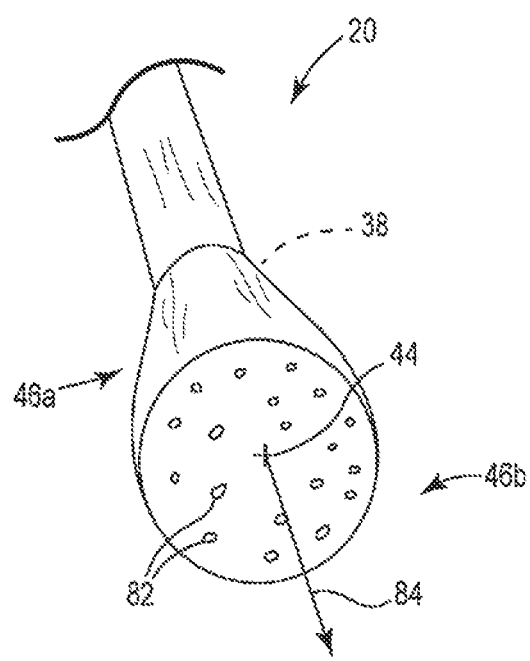
FIG. 5 is a perspective view showing an example composite balloon in accordance with an illustrative embodiment.

FIG. 5 is a perspective view showing an example composite balloon 20 that has been treated using the method 70 of FIG. 4. As can be seen in FIG. 5, the distal section 46b of the balloon 20 includes a plurality of micropores 82 which, due to the size and shape of the distal section 46b in its inflated state, face substantially in a distal direction away from the distal end 44 of the balloon 20 in the direction indicated generally by arrow 84. When a steady flow of electrically conductive fluid is provided to the interior section 38 of the balloon 20, at least a portion of the fluid 30 seeps through the micropores 82 and into contact with body tissue located distally of the balloon 20. The proximal section 46a of the balloon 20 is substantially non-porous, and thus prohibits the flow of pressurized fluid through the proximal section 46a.

Figure 6:
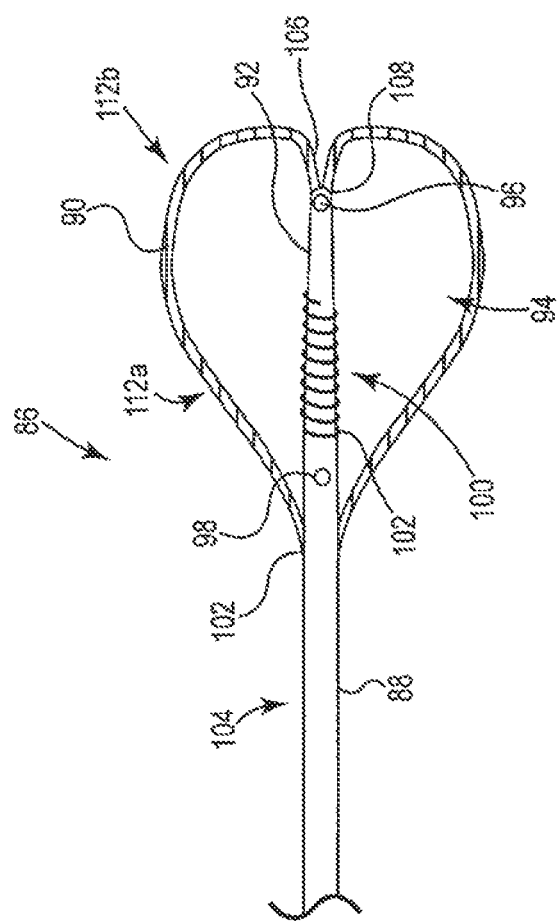
FIG. 6 is a partial cross-sectional view showing the distal section of an ablation device in accordance with another illustrative embodiment.

FIG. 6 is a partial cross-sectional view showing the distal section of an ablation device 86 in accordance with another illustrative embodiment. The ablation device 86 includes an elongate shaft 88 coupled to an inflatable ablation balloon 90. The proximal section of the shaft 88 (not shown) is coupled to an electrically conductive fluid source and an RF generator. In the embodiment of FIG. 6, the distal section 92 of the shaft 88 extends through the interior 94 of the balloon 90, and includes a number of fluid ports 96, 98 for circulating fluid through the balloon interior 94. A first fluid port 96 in fluid communication with a first lumen within the shaft 88 is configured to deliver electrically conductive fluid from an external fluid source into the balloon interior 94. A second fluid port 98 in fluid communication with a return fluid lumen of the shaft 88, in turn, functions as a return port for recirculating heated fluid within the balloon interior 94 to a location outside of the patient's body for cooling.

An electrode assembly 100 disposed within the interior 94 of the balloon 90 is electrically coupled to an RF generator, and is configured to generate an RF electric field for creating controlled lesions within tissue located adjacent to the balloon 90. In some embodiments, and as shown in FIG. 6, the electrode assembly 100 comprises a metal coil RF electrode 102 having a helical shape that extends about a portion of the shaft 88 located within the balloon interior 94. In other embodiments, the RF electrode 102 can comprise a tubular member, ring, flat ribbon, or other suitable shape. In some embodiments, the electrode assembly 100 can include multiple electrodes 102 as part of either a bipolar RF ablation system, or as part of a unipolar system with multiple electrodes.

In the embodiment of FIG. 6, a proximal section 112a of the balloon 90 is coupled to the distal section 92 of the elongate shaft 88. A distal section 112b of the balloon 90, in turn, is coupled to the distal end 108 of the elongate shaft 88. In some embodiments, and as shown in FIG. 6, the distal section 112b of the balloon 90 has an invaginated configuration created by folding or turning a portion of the balloon 90 back upon itself and attaching the distal end 106 of the balloon 90 to an interior surface of the shaft distal end 108. The balloon 90 is inflatable from an initial, collapsed position having a low-profile that facilitates traversal of the device 86 through the body, to a second, expanded position that contacts and engages the body tissue to be ablated. In some embodiments, the balloon 90 has a composite structure formed from different polymeric materials, which helps to direct and focus the RF energy from the RF electrode 100 into body tissue located at or near a distal section 112b of the balloon 90. In one embodiment, for example, the composite balloon 90 includes a proximal, non-conductive section 112a made from a hydrophobic polymer and a distal, conductive section 112b made from a hydrophilic polymer. In some embodiments, for example, the composite balloon structure can comprise a proximal section 112a made from a hydrophobic polyurethane material such as TECOPHILIC 60D-35® and a distal section 112b made from a hydrophilic polyurethane material such as TECOPHILIC 60D®. Other polymeric materials can also be used to impart differing hydrophilic characteristics to the proximal and distal sections 112a, 112b, as desired.

When inflated with an electrically conductive fluid, the distal section 112b of the balloon 90 is rendered conductive by hydration due to the ionic content of the fluid when RF energy is supplied to the RF electrode 102. An electrical current is thus transmitted through the fluid and into the tissue in contact with the distal section 112b of the balloon 90. When inflated, the invaginated configuration of the balloon 90 also serves to direct the RF electrical field towards the distal section 112b of the balloon 90.

The ablation device 86 can further include one or more features described with respect to other embodiments, including one or more temperature sensors for sensing the temperature of fluid within or on the surface of the balloon 90, and one or more electrocardiogram sensors for sensing electrical activity in or near the heart. The device 86 can also include other features such as a spring-actuated plunger assembly. In certain embodiments, the balloon 90 can also be made permeable or semi-permeable, allowing at least some of the pressurized fluid within the interior section 94 of the balloon 90 to seep into the body at or near the target ablation site.

Figure 7:
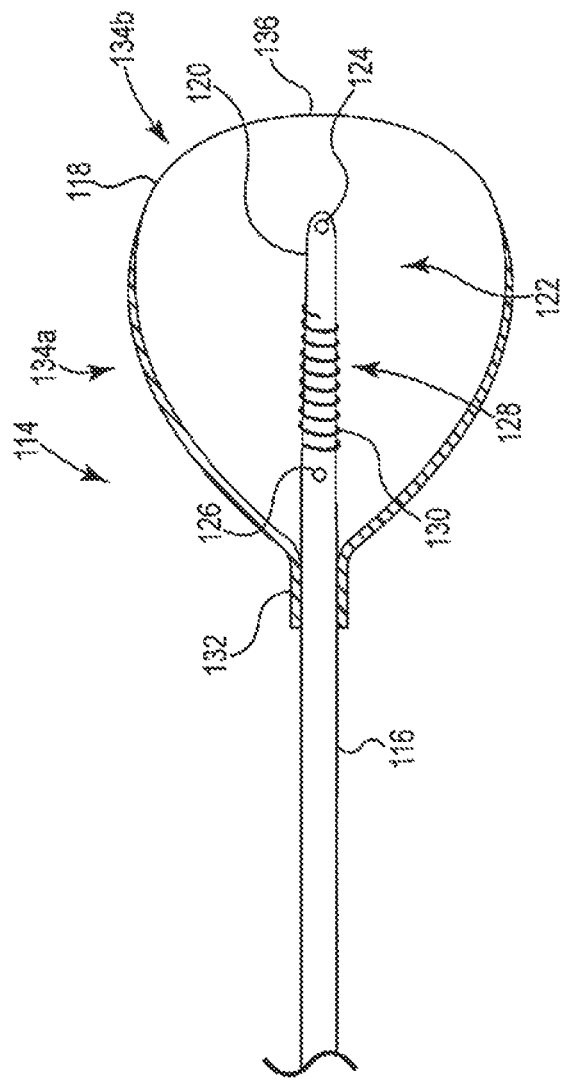
FIG. 7 is a partial cross-sectional view showing the distal section of an ablation device in accordance with another illustrative embodiment.

FIG. 7 is a partial cross-sectional view showing the distal section of an ablation device 114 in accordance with another illustrative embodiment. The ablation device 114 includes an elongate shaft 116 coupled to an inflatable ablation balloon 118. The proximal section of the shaft 116 is coupled to an electrically conductive fluid source and an RF generator. In the embodiment of FIG. 7, the distal section 120 of the shaft 116 extends through the interior 122 of the balloon 118, and includes a number of fluid ports 124, 126 for circulating fluid through the balloon interior 122. A first fluid port 124 in fluid communication with a first lumen within the shaft 116 is configured to deliver electrically conductive fluid from an external fluid source into the balloon interior 122. A second fluid port 126 in fluid communication with a return fluid lumen within the shaft 116, in turn, functions as a return port for recirculating heated fluid within the balloon interior 122 to a location outside of the patient's body for cooling.

An electrode assembly 128 disposed within the interior 122 of the balloon 118 is electrically coupled to an RF generator, and is configured to generate an RF electric field for creating controlled lesions within tissue located adjacent to the balloon 118. In some embodiments, and as shown in FIG. 7, the electrode assembly 128 comprises a metal coil RF electrode 130 having a helical shape that extends about a portion of the shaft 116 located within the balloon interior 122. In other embodiments, the RF electrode 130 can comprise a tubular member, ring, flat ribbon, or other suitable shape. In some embodiments, the electrode assembly 128 can include multiple electrodes 130 as part of either a bipolar RF ablation system, or as part of a unipolar system with multiple electrodes.

In the embodiment of FIG. 7, a proximal end portion 134 of the balloon 118 is coupled to the distal section 120 of the elongate shaft 118. The balloon 118 is inflatable from an initial, collapsed position having a low-profile that facilitates traversal of the device 114 through the body, to a second, expanded position that contacts and engages the body tissue to be ablated. In some embodiments, and as shown, the thickness of the balloon 118 can taper along a length of the balloon 118 that is generally parallel with the shaft 116 such that the thickness of the proximal section 134a is greater than the thickness of the distal section 134b. In certain embodiments, the thickness of the balloon 118 tapers continuously along the length of the balloon 118 between the proximal and distal sections 134a, 134b. In one embodiment, for example, the balloon 118 may continuously taper from a thickness of between about 5 mils (0.005 inches) to 15 mils (0.015 inches) at or near the location 132 where the proximal section 134a of the balloon 118 attaches to the elongate shaft 116, to a thickness of between about 0.5 mil to 5 mils at or near a distal end portion 136 of the balloon 118.

In other embodiments, the balloon 118 may transition in thickness at one or more discrete locations along the length of the balloon 118 such that the thickness of the proximal section 134a is greater than the thickness of the distal section 134b. In one embodiment, for example, the balloon 118 thickness may transition from a relatively thick configuration at the proximal portion 134a of the balloon 118 to a relatively thin configuration at the distal section 134b of the balloon 118 at a location substantially midway along the length of the balloon 118. The balloon 118 may also stepwise transition in thickness at multiple locations along the proximal and/or distal sections 134a, 136b of the balloon 118. Other configurations are also possible.

The balloon 118 can comprise a hydrophilic polymer that facilitates the transmission of the electromagnetic field generated by the RF electrode 130 through the balloon material and into contact with the tissue. In some embodiments, the balloon 118 comprises a composite structure in which multiple materials are used to transition the balloon 118 from a relatively hydrophobic composition along proximal section 134a of the balloon 118 to a relatively hydrophilic composition along the distal section 134b of the balloon 118. In some embodiments, for example, the composite balloon structure can comprise a proximal section 134a made from a hydrophobic polyurethane material such as TECOPHILIC 60D-35® and a distal section 134b made from a hydrophilic polyurethane material such as TECOPHILIC 60D®, as discussed herein. The resulting structure is a composite balloon 118 that transitions both in material composition and in thickness along the length of the balloon 118. During an ablation, this reduction in thickness, (and in some embodiments also a change in material composition) along the length of the balloon 118 causes a greater amount of the electric field generated by the RF electrode 130 to pass through the distal section 134b of the balloon 118, allowing the clinician to target body tissue that is situated distally of the balloon 118.

The ablation device 114 can further include one or more features described with respect to other embodiments herein, including one or more temperature sensors for sensing the temperature of fluid within or on the outer surface of the balloon 118 and/or one or more electrocardiogram sensors for sensing electrical activity in or near the heart. The device 114 can also include other features such as a spring-actuated plunger assembly. In certain embodiments, the balloon 118 can also be made permeable or semi-permeable, allowing at least some of the pressurized fluid within the interior section 122 of the balloon 118 to seep into the body at or near the target ablation site.

Figure 8:
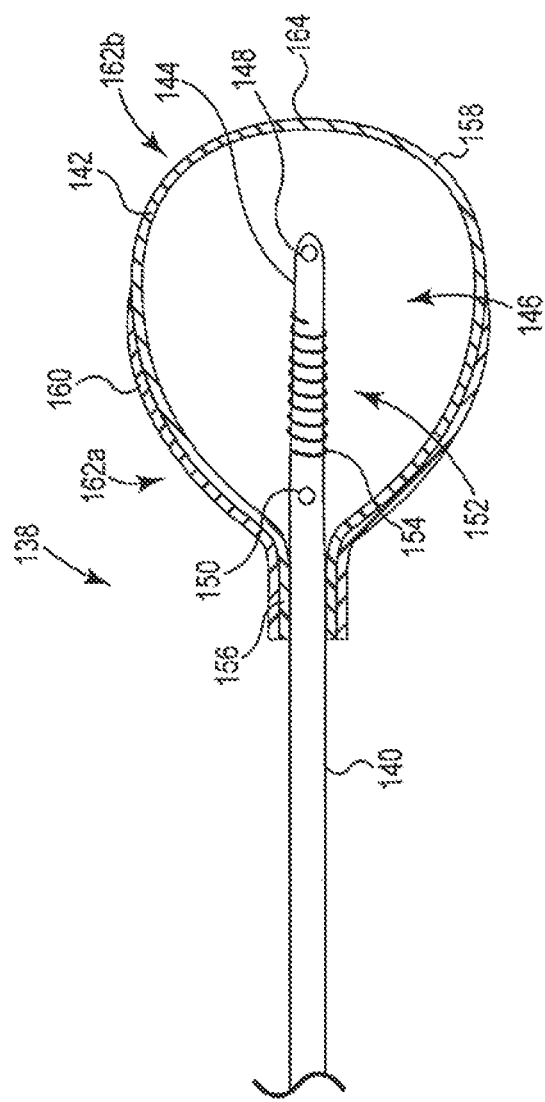
FIG. 8 is a partial cross-sectional view showing the distal section of an ablation device in accordance with another illustrative embodiment.

FIG. 8 is a partial cross-sectional view showing the distal section of an ablation device 138 in accordance with another illustrative embodiment. The ablation device 138 includes an elongate shaft 140 coupled to an inflatable ablation balloon 142. The proximal section of the shaft 140 is coupled to an electrically conductive fluid source and an RF generator. In the embodiment of FIG. 8, the distal section 144 of the shaft 140 extends through the interior 146 of the balloon 142, and includes a number of fluid ports 148, 150 for circulating fluid through the balloon interior 146. A first fluid port 148 in fluid communication with a first lumen within the shaft 140 is configured to deliver electrically conductive fluid from an external fluid source into the balloon interior 146. A second fluid port 150 in fluid communication with a return fluid lumen within the shaft 140, in turn, functions as a return port for recirculating heated fluid within the balloon interior 146 to a location outside of the patient's body for cooling.

An electrode assembly 152 disposed within the interior 146 of the balloon 142 is electrically coupled to an RF generator, and is configured to generate an RF electric field for creating controlled lesions within tissue located adjacent to the balloon 142. In some embodiments, and as shown in FIG. 8, the electrode assembly 152 comprises a metal coil RF electrode 154 having a helical shape that extends about a portion of the shaft 140 located within the balloon interior 146. In other embodiments, the RF electrode 154 can comprise a tubular member, ring, flat ribbon, or other suitable shape. In some embodiments, the electrode assembly 152 can include multiple electrodes 154 as part of either a bipolar RF ablation system, or as part of a unipolar system with multiple electrodes.

In the embodiment of FIG. 8, a proximal end portion 156 of the balloon 142 is coupled to the distal section 144 of the elongate shaft 140. The balloon 142 is inflatable from an initial, collapsed position having a low-profile that facilitates traversal of the device 138 through the body, and a second, expanded position that contacts and engages the body tissue to be ablated. In some embodiments, and as shown in FIG. 8, the balloon 142 comprises a multi-layered structure having a first layer 158 and a second layer 160. The first layer 158 of the balloon 142 comprises a hydrophilic hydratable, ionically conductive material layer that extends across the entire surface area of the balloon 142, along both a proximal section 162a and a distal section 162b of the balloon 142. In certain embodiments, for example, the first layer 158 comprises a hydrophilic polyurethane material such a TECOPHILIC 60D®. In certain embodiments, the thickness of the first layer 158 is between about 1 mil to 3 mils.

In some embodiments, first layer 158 has a uniform thickness along the entire length of the balloon 142. In other embodiments, the thickness of the first layer 158 may transition in thickness along the length of the balloon 142. For example, in some embodiments, the first layer 158 of the balloon 142 may taper in thickness along the length of the balloon 142 such that the portion of first layer 158 located along the proximal section 162a of the balloon 142 is thicker than the portion of the first layer 158 located along the distal section 162b. The thickness of the first layer 158 can taper either continuously or at one or more discrete locations along the length of the balloon 142. In some embodiments, the thickness of the first layer 158 may transition in thickness from about 3 mils at or near the location where the proximal end portion 156 of the balloon 142 attaches to the elongate shaft 140 to a thickness of about 1 mil at or near the distal end portion 164 of the balloon 142.

The second layer 160 of the balloon 142 comprises a hydrophobic material, and extends across only a portion of the balloon 142. In the embodiment of FIG. 8, for example, the second layer 160 is located along only the proximal section 162a of the balloon 142. In some embodiments, the second layer 160 comprises a hydrophobic polymer mask that is spray-coated onto the first layer 158 during the balloon manufacturing process. An example hydrophobic material that can be used to form the second layer 160 comprises TECOPHILIC 60D-35®. Other techniques can also be used for forming the second layer 160, including sputtering, adhesion, or co-extrusion.

In the embodiment of FIG. 8, the thickness of the second layer 160 tapers continuously along its length. In other embodiments, the second layer 160 reduces in thickness at one or more discrete locations along its length. In some embodiments, the thickness of the second layer 160 may transition from between about 5 mils at or near the location where the proximal end portion 156 of the balloon 142 attaches to the elongate shaft 140 to a thickness of about 1 mil at or near the location where the second layer 160 terminates.

During ablation, the presence of the hydrophobic second layer 160 over the first layer 158 of the balloon 142 causes a greater amount of the electrical field generated by the RF electrode 154 to pass through the distal section 162b of the balloon 142, allowing the clinician to target body tissue that is situated distally of the balloon 142. In some cases during ablation, the presence of the hydrophobic second layer 160 over the first layer 158 of the balloon 142 causes the RF current to be concentrated and evenly distributed through only the unmasked hydrophilic distal surface of the balloon, allowing the clinician to target body tissue that is situated distally of the balloon 142.

The ablation device 138 can further include one or more features described with respect to other embodiments, including one or more temperature sensors for sensing the temperature of fluid within or on the surface of the balloon and/or one or more electrocardiogram sensors for sensing electrical activity in or near the heart. The device 138 can also include other features such as a spring-actuated plunger assembly. In certain embodiments, the balloon 142 can also be made permeable or semi-permeable, allowing at least some of the pressurized fluid within the interior 146 of the balloon 142 to seep into the body at or near the target ablation site.

Figure 9:
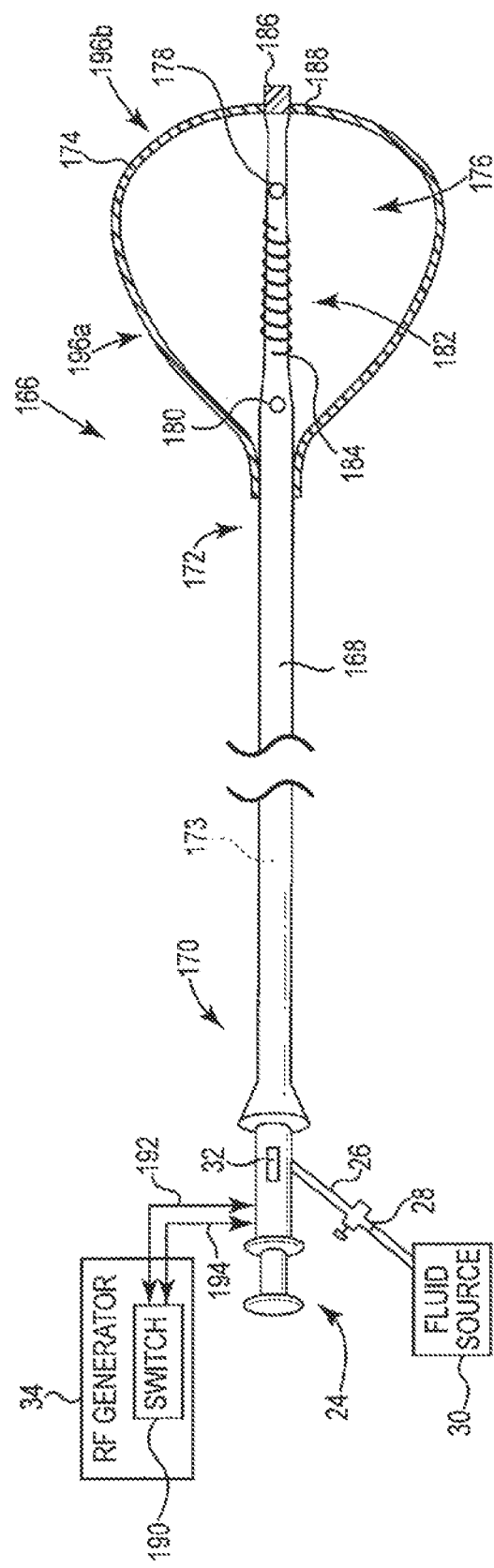
FIG. 9 is a schematic view of an ablation device in accordance with another illustrative embodiment.

FIG. 9 is a schematic view of an ablation device 166 in accordance with another illustrative embodiment. The ablation device 166 includes an elongate shaft 168 having a proximal section 170, a distal section 172, and at least one lumen 173 extending through the shaft 168 between the proximal and distal sections 170, 172. An inflatable balloon 174 coupled to the distal section 172 of the shaft 168 can be inflated at a target location within the body and brought into contact with the body tissue to be treated. In the embodiment of FIG. 9, the distal section 172 of the shaft 168 extends through an interior 176 of the balloon 174, and includes a number of fluid ports 176, 178 for circulating fluid through the balloon interior 176. A first fluid port 178 in fluid communication with a first lumen within the shaft 168 is configured to deliver electrically conductive fluid from an external fluid source into the balloon interior 176. A second fluid port 180 in fluid communication with a return fluid lumen within the shaft 168, in turn, functions as a return port for recirculating heated fluid within the balloon interior 176 to a location outside of the patient's body for cooling.

An electrode assembly 182 disposed within the interior 176 of the balloon 174 is electrically coupled to an RF generator 34 that can be used to generate an RF electric field for creating controlled lesions within tissue. In the embodiment of FIG. 9, the electrode assembly 182 includes a first electrode 184 and a second electrode 186. The first electrode 184 comprises a metal coil RF electrode having a helical shape that extends about a portion of the shaft 168 located within the balloon interior 176. In other embodiments, the first electrode 184 can comprise a tubular member, ring, flat ribbon, or other suitably shaped electrode. The second electrode 186, in turn, is coupled to the distal end portion 188 of the elongate shaft 168, and is located outside of the balloon 174 and directly contacts the body tissue to be ablated.

In some embodiments, the RF generator 34 includes a switch 190 for selectively activating either the first electrode 184 or the second electrode 186. In one embodiment, and as shown, the switch 190 includes a first electrical wire 192 electrically coupled to the first electrode 184 and a second electrical wire 194 electrically coupled to the second electrode 186. During an ablation procedure, the ability to switch back and forth between the first and second electrodes 184, 186 allows the operator to adjust between providing ablation over a relatively large area via conduction through the balloon 174 or over a relatively small, focused area via the second electrode 186, which is in direct contact with the tissue and which has a smaller contact surface area than the balloon 174.

In the embodiment of FIG. 9, a proximal section 196a of the balloon 174 is coupled to the distal section 172 of the elongate shaft 168. A distal section 196b of the balloon 174, in turn, is coupled to the distal end 188 of the elongate shaft 168. In certain embodiments, the balloon 166 has a composite structure formed from different polymeric materials. In one embodiment, for example, the composite balloon 166 includes a proximal, non-conductive section 196a made from a hydrophobic polymer and a distal, hydratable ionically conductive section 196b made from a hydrophilic polymer. In some embodiments, for example, the composite balloon structure can comprise a proximal section 196a made from a hydrophobic polyurethane material such as TECOPHILIC 60D-35® and a distal section 196b made from a hydrophilic polyurethane material such as TECOPHILIC 60D®. Other polymeric materials can be used to impart differing hydrophilic characteristics to the proximal and distal sections 196a, 196b.

When inflated with an electrically conductive fluid, the distal section 196b of the balloon 174 is rendered conductive by hydration due to the ionic content of the fluid when the RF energy is supplied to the first RF electrode 184. As a result, electrical current is transmitted through the fluid and into the tissue in contact with the distal section 196b of the balloon 174.

The ablation device 166 can further include one or more features described with respect to other embodiments, including one or more temperature sensors for sensing the temperature of fluid within the balloon or on the surface of the balloon at the balloon-tissue interface, and one or more electrocardiogram sensors for sensing electrical activity in or near the heart. The device 166 can also include other features such as a spring-actuated plunger assembly. In certain embodiments, the balloon 174 can also be made semi-permeable, allowing at least some of the pressurized fluid within the interior section 176 the balloon 174 to seep into the body at or near the target ablation site.

Figure 10:
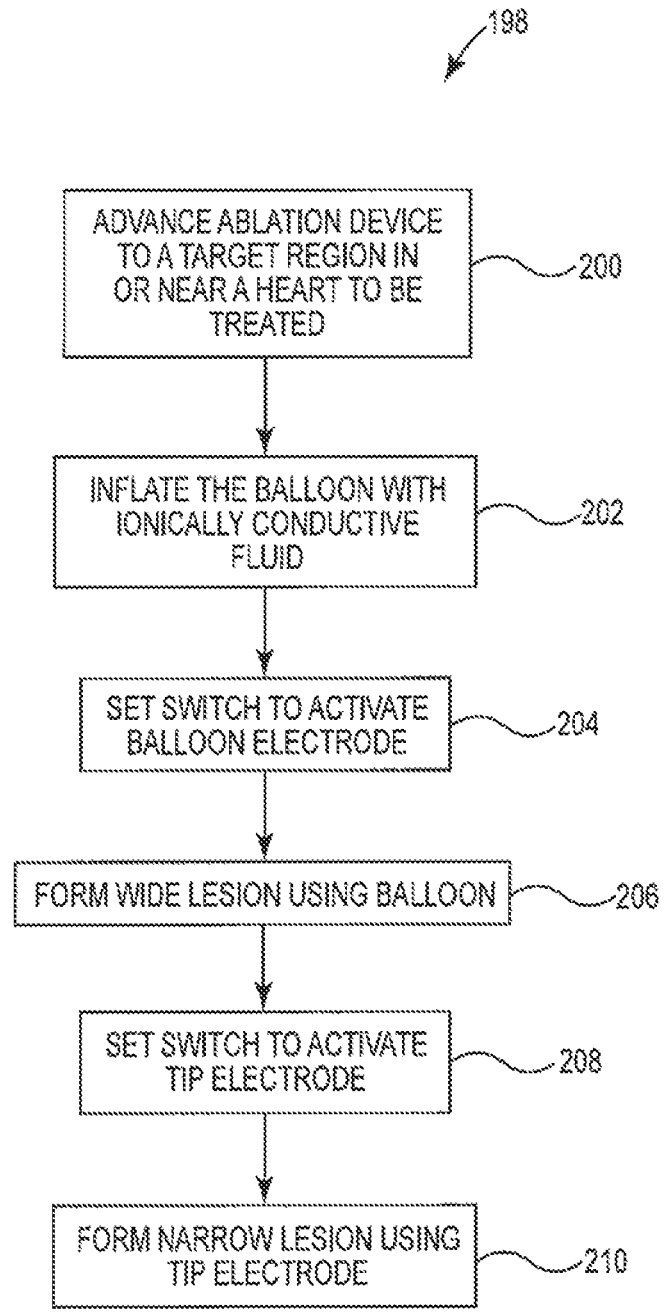
FIG. 10 is a flow diagram of an illustrative method of performing a cardiac ablation procedure using the ablation device of FIG. 9.

FIG. 10 is a flow diagram of an illustrative method 198 of performing an ablation procedure of using an ablation device. FIG. 10 may represent, for example, several example steps that can be used in conjunction with the ablation device 166 of FIG. 9 for performing ablation on cardiac tissue. The method 198 can be performed using any of the ablation devices described herein, and can be used for performing other types of ablation therapy. In one embodiment, for example, the method 198 can be used for performing ablation therapy on brain tissue for treating neurological disorders such as Parkinson's disease.

To perform the therapy, a clinician inserts the ablation device 166 into the lumen of a guide catheter, and advances the ablation device 166 to a region in or near the heart to be treated (block 200). In the treatment of paroxysmal atrial fibrillation, for example, the clinician may insert the guide catheter and ablation device into a main vein or artery (e.g., a femoral artery), and advance the assembly through the vasculature into position within a heart chamber or cardiac vessel to be treated (e.g., a pulmonary vein). In some embodiments, a steering mechanism within the guide catheter or within the ablation device 166 itself can be used to steer the distal end of the device 166 into position to the desired treatment site.

Once in position, an electrically conductive fluid is then injected into the balloon 174, causing the balloon 174 to inflate (block 202). If necessary, the switch 190 on the RF generator 34 can then be set to activate the first (i.e., balloon) electrode 184 (block 204), causing energy to flow from the electrode 184 to the distal conductive section 196b of the balloon 174 through conduction through the fluid and balloon material. The clinician may then form a relatively wide lesion on the tissue by contacting the distal section 196b of the balloon 174 with the tissue (block 206).

The size and shape of the distal balloon section 196b produces a lesion that is very uniform in nature and is void of dehydrated or charred areas that can result in catheters that use an electrode in direct contact with the tissue to be ablated. In some procedures, the size and shape of the inflated balloon 174 can also facilitate forming overlapping lesions to ensure a contiguous ablation line is created and that the aberrant electrical conduction is completely blocked. In those embodiments in which the distal section 196b is also porous, a steady flow of electrically conductive fluid can be maintained throughout the ablation period, which further serves to create an electrical pathway between the balloon 174 and the body tissue.

If, during the ablation procedure, the operator desires to provide a pin-point lesion on the tissue, the switch 190 can then be set to operate using the second electrode 186 (block 208). Once set, the energy from the RF generator 34 is then transmitted to the second (i.e., tip) electrode 186, which directs RF energy directly into the tissue. In contrast to the first electrode 184, which has a relatively large surface area in contact with the tissue to be ablated, the second electrode 186 produces a smaller, focused ablation (block 210). In certain procedures, for example, the second electrode 186 can be used to generate narrow, focused ablation points whereas the first electrode 184 can be used to generate wider, less-focused ablation points. The process of switching back and forth between each of the electrodes 184, 186 can be repeated one or more times until the ablation procedure is complete.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for performing ablation therapy on the body of a patient, the method comprising:
   advancing an ablation device to a target body tissue region, the ablation device including an inflatable balloon coupled to an elongate shaft, a first electrode disposed within an interior space of the balloon, and a second electrode located outside of the balloon;
   injecting an electrically conductive fluid into the interior section of the balloon and inflating the balloon from a collapsed state to an expanded state within the body;
   selectively energizing the first electrode and generating a first RF electrical field within the balloon interior;
   forming at least one ablation lesion within the body tissue using the first RF electrical field;
   selectively energizing the second electrode and generating a second RF electrical field; and
   forming at least one ablation lesion within the body tissue using the second RF electrical field.

2. The method of claim 1, further comprising an RF generator including a switching mechanism, and wherein selectively energizing the first or second electrodes includes operating the switching mechanism between a first and second switch position.

3. The method of claim 1, wherein forming at least one ablation lesion within the body tissue using the first RF electrical field includes forming a lesion in the body tissue at a location distal to the elongate shaft.

4. The method of claim 1, wherein the at least one ablation lesion formed within the body tissue using the first RF electric field is larger than the at least one ablation lesion formed in the body tissue using the second RF electric field.

5. The method of claim 1, wherein the balloon further comprises a temperature sensor disposed within an interior space of the balloon, the method further comprising sensing a temperature of the electrically conductive fluid.

6. The method of claim 1, wherein the balloon further comprises a temperature sensor located outside the balloon, the method further comprising sensing a temperature of the target body tissue region.

7. The method of claim 1, wherein the inflatable balloon is comprised of a material that allows the electrically conductive fluid to permeate through the balloon and wherein injecting an electrically conductive fluid comprises continuously injecting an electrically conductive fluid into the balloon so that the balloon remains in the expanded state.

8. The method of claim 7, further comprising: determining an amount of electrically conductive fluid injected into the balloon.

9. The method of claim 7, wherein the electrically conductive fluid includes a drug.

10. A method for performing ablation therapy using an ablation device, the method comprising:
    advancing an ablation device to a tissue region in a body of a patient, the ablation device including an inflatable balloon coupled to a distal end of an elongate shaft, the inflatable balloon including a conductive section, a first electrode disposed within an interior space of the balloon and a second electrode located outside of the balloon;
    injecting an electrically conductive fluid into the balloon to inflate the balloon to an expanded state, wherein at least one of the conductive section and the second electrode contact the tissue region; and
    activating at least one of the first electrode and the second electrode to ablate at least a portion of the contacted tissue region.

11. The method of claim 10, further comprising a RF generator including a switching mechanism, wherein activating the first electrode includes operating the switching mechanism to a first switch position and wherein activating the second electrode includes operating the switching mechanism to a second switch position.

12. The method of claim 10, wherein the inflatable balloon further comprises at least one temperature sensor, the method further comprising sensing a temperature of at least one of the electrically conductive fluid and the tissue region using the temperature sensor.

13. The method of claim 12, wherein the temperature is sensed while activating at least one of the first electrode and the second electrode.

14. The method of claim 10, wherein the inflatable balloon is comprised of a material that allows the electrically conductive fluid to permeate through the balloon and wherein injecting an electrically conductive fluid comprises continuously injecting an electrically conductive fluid into the balloon so that the balloon has a substantially constant internal pressure.

15. The method of claim 14, further comprising determining an amount of electrically conductive fluid injected into the balloon.

16. The method of claim 14, wherein the electrically conductive fluid includes a drug.

17. The method of claim 10, wherein a surface area of the electrically conductive region is larger than a surface area of the second electrode.

18. A method for performing ablation therapy on the body of a patient, the method comprising:
advancing an ablation device to a target body tissue region, the ablation device including an inflatable balloon coupled to a distal end of an elongate shaft, the inflatable balloon including a conductive section and a first electrode disposed within an interior space of the balloon;
injecting an electrically conductive fluid into the balloon to inflate the balloon to an expanded state, wherein the conductive section of the balloon contacts a portion of the target body tissue region; and
generating a current through the electrically conductive fluid using the first electrode to ablate a portion of the target body tissue region.

19. The method of claim 18, the ablation device further including a second electrode located outside of the balloon, wherein a surface area of the second electrode is smaller than a surface area of the conductive section, the method further comprising: energizing the second electrode to ablate a portion of the target body tissue region.

20. The method of claim 19, further comprising a RF generator including a switching mechanism, wherein generating a current through the electrically conductive fluid using the first electrode includes operating the switching mechanism to a first switch position and wherein energizing the second electrode includes operating the switching mechanism to a second switch position.

* * * * *